(12) United States Patent
Pereira et al.

(10) Patent No.: US 12,220,334 B2
(45) Date of Patent: *Feb. 11, 2025

(54) STENT-CONTAINING MEDICAL DEVICES AND METHODS OF USING THE SAME

(71) Applicant: Boston Scientific Scimed, Inc., Maple Grove, MN (US)

(72) Inventors: Peter J. Pereira, Mendon, MA (US); Claude O. Clerc, Marlborough, MA (US); Gerald Fredrickson, Westford, MA (US); Jonathan Zoll, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 148 days.

This patent is subject to a terminal disclaimer.

(21) Appl. No.: 17/873,712

(22) Filed: Jul. 26, 2022

(65) Prior Publication Data
US 2022/0354672 A1 Nov. 10, 2022

Related U.S. Application Data

(63) Continuation of application No. 14/753,201, filed on Jun. 29, 2015, now Pat. No. 10,610,386.
(Continued)

(51) Int. Cl.
*A61F 2/848* (2013.01)
*A61F 2/89* (2013.01)
(Continued)

(52) U.S. Cl.
CPC .......... *A61F 2/848* (2013.01); *A61F 2/89* (2013.01); *A61F 2/94* (2013.01); *A61F 2/958* (2013.01); *A61L 31/10* (2013.01); *A61L 31/14* (2013.01)

(58) Field of Classification Search
CPC ...... A61F 2/06; A61F 2/07; A61F 2/82; A61F 2/848; A61F 2/89; A61F 2/94;
(Continued)

(56) References Cited

U.S. PATENT DOCUMENTS

| 4,770,176 A | 9/1988 | McGreevy et al. |
| 5,100,429 A | 3/1992 | Sinofsky et al. |

(Continued)

FOREIGN PATENT DOCUMENTS

| CN | 1341032 A | 3/2002 |
| CN | 102743210 A | 10/2012 |

(Continued)

OTHER PUBLICATIONS

Chan et al; "Enhancement of Porcine Skin Graft Adherence using a Light-Activated Process," Journal of Surgical Research vol. 108, pp. 77-84, 2002.

(Continued)

*Primary Examiner* — Ryan J. Severson
(74) *Attorney, Agent, or Firm* — Seager, Tufte & Wickhem LLP (57) ABSTRACT

The present disclosure pertains to medical devices that comprise a stent body having two ends, a central region therebetween, and comprising structural elements extending around the stent body and a covering material disposed over the stent body, the covering material covering only a portion of the stent body, in which the covering material is provided with a plurality of openings that provide areas where the stent body is not covered by the covering material. The present disclosure further pertains to medical apparatuses that comprise such medical devices and methods of treatment using such medical devices.

19 Claims, 5 Drawing Sheets

Related U.S. Application Data (60) Provisional application No. 62/018,262, filed on Jun. 27, 2014.

(51) Int. Cl.
*A61F 2/94* (2013.01)
*A61F 2/958* (2013.01)
*A61L 31/10* (2006.01)
*A61L 31/14* (2006.01)

(58) Field of Classification Search
CPC .......... A61F 2/945; A61F 2/958; A61F 2/962; A61F 2/966; A61L 31/08; A61L 31/10; A61L 31/14; A61L 27/507
See application file for complete search history.

(56) References Cited

U.S. PATENT DOCUMENTS

| | | | |
|---|---|---|---|
| 5,178,618 A | 1/1993 | Kandarpa | |
| 5,195,984 A * | 3/1993 | Schatz | A61F 2/958 604/103.05 |
| 5,389,106 A * | 2/1995 | Tower | A61F 2/88 606/198 |
| 5,549,663 A | 8/1996 | Cottone, Jr. | |
| 5,575,815 A | 11/1996 | Slepian et al. | |
| 5,593,403 A | 1/1997 | Buscemi | |
| 5,683,453 A | 11/1997 | Palmaz | |
| 5,741,327 A | 4/1998 | Frantzen | |
| 5,769,883 A | 6/1998 | Buscemi et al. | |
| 5,769,887 A * | 6/1998 | Brown | A61F 2/958 606/198 |
| 5,849,035 A | 12/1998 | Pathak et al. | |
| 5,851,231 A | 12/1998 | Wolff et al. | |
| 5,989,244 A | 11/1999 | Gregory et al. | |
| 5,997,517 A | 12/1999 | Whitbourne | |
| 6,004,943 A | 12/1999 | Shi et al. | |
| 6,087,552 A | 7/2000 | Gregory | |
| 6,176,871 B1 | 1/2001 | Pathak et al. | |
| 6,183,506 B1 | 2/2001 | Penn et al. | |
| 6,254,627 B1 | 7/2001 | Freidberg | |
| 6,391,052 B2 | 5/2002 | Buirge et al. | |
| 6,436,132 B1 * | 8/2002 | Patel | A61F 2/07 623/1.13 |
| 6,451,373 B1 | 9/2002 | Hossainy et al. | |
| 6,497,671 B2 | 12/2002 | Ferrera et al. | |
| 6,579,314 B1 | 6/2003 | Lombardi et al. | |
| 6,585,773 B1 | 7/2003 | Xie | |
| 6,613,084 B2 | 9/2003 | Yang | |
| 6,673,102 B1 | 1/2004 | Vonesh et al. | |
| 6,733,768 B2 | 5/2004 | Hossainy et al. | |
| 6,890,339 B2 | 5/2005 | Sahatjian et al. | |
| 6,986,899 B2 | 1/2006 | Hossainy et al. | |
| 7,001,328 B1 | 2/2006 | Barofsky et al. | |
| 7,004,966 B2 * | 2/2006 | Edwin | B29C 65/48 623/1.13 |
| 7,179,286 B2 | 2/2007 | Lenz | |
| 7,195,640 B2 | 3/2007 | Falotico et al. | |
| 7,311,727 B2 | 12/2007 | Mazumder et al. | |
| 7,318,836 B2 | 1/2008 | Brown et al. | |
| 7,572,288 B2 * | 8/2009 | Cox | A61F 2/82 623/1.15 |
| 7,591,841 B2 | 9/2009 | Hossainy et al. | |
| 7,959,942 B2 | 6/2011 | Cottone | |
| 7,981,150 B2 | 7/2011 | Scheuermann et al. | |
| 8,147,538 B2 | 4/2012 | Brown et al. | |
| 8,211,168 B2 | 7/2012 | Purdy et al. | |
| 8,252,040 B2 * | 8/2012 | Cox | A61B 17/12022 623/1.13 |
| 8,642,068 B2 | 2/2014 | Cottone | |
| 8,790,241 B2 * | 7/2014 | Edwin | B29C 65/48 623/1.13 |
| 8,870,909 B2 * | 10/2014 | Cox | A61B 17/12113 623/1.15 |
| 9,474,575 B2 | 10/2016 | Sargeant | |
| 9,498,322 B2 | 11/2016 | Thomas | |
| 9,603,975 B2 | 3/2017 | Fredrickson et al. | |
| 9,622,753 B2 * | 4/2017 | Cox | A61B 17/12113 |
| 9,867,687 B2 | 1/2018 | Sargeant | |
| 9,943,399 B2 | 4/2018 | McGhie | |
| 10,610,386 B2 | 4/2020 | Pereira et al. | |
| 11,413,170 B2 * | 8/2022 | Pereira | A61F 2/94 |
| 2001/0000188 A1 * | 4/2001 | Lenker | A61F 2/07 623/1.13 |
| 2001/0034550 A1 | 10/2001 | Buirge et al. | |
| 2002/0022876 A1 | 2/2002 | Richter et al. | |
| 2002/0090398 A1 | 7/2002 | Dunn et al. | |
| 2002/0143384 A1 | 10/2002 | Ozasa | |
| 2003/0139802 A1 * | 7/2003 | Wulfman | A61B 17/12022 623/1.15 |
| 2003/0144725 A1 | 7/2003 | Lombardi | |
| 2003/0204245 A1 * | 10/2003 | Brightbill | A61F 2/915 623/1.34 |
| 2004/0133274 A1 | 7/2004 | Webler | |
| 2004/0167615 A1 | 8/2004 | Lenz | |
| 2004/0176832 A1 | 9/2004 | Hartley et al. | |
| 2006/0271151 A1 | 11/2006 | McGarry et al. | |
| 2007/0219619 A1 | 9/2007 | Dieck et al. | |
| 2007/0225799 A1 | 9/2007 | Doty | |
| 2008/0097575 A1 | 4/2008 | Cottone | |
| 2008/0243243 A1 | 10/2008 | Williams et al. | |
| 2008/0319259 A1 | 12/2008 | Goto | |
| 2009/0187240 A1 | 7/2009 | Clerc et al. | |
| 2010/0049294 A1 | 2/2010 | Zukowski et al. | |
| 2011/0152898 A1 | 6/2011 | Kochevar et al. | |
| 2012/0059455 A1 | 3/2012 | Weber et al. | |
| 2012/0165920 A1 | 6/2012 | Meyer et al. | |
| 2012/0172972 A1 | 7/2012 | Meyer et al. | |
| 2012/0226346 A1 | 9/2012 | Biosmier et al. | |
| 2012/0271290 A1 | 10/2012 | Sargeant | |
| 2013/0172988 A1 | 7/2013 | Kutryk et al. | |
| 2015/0351767 A1 | 12/2015 | Zoll et al. | |
| 2015/0374516 A1 | 12/2015 | Pereira et al. | |
| 2016/0166739 A1 | 6/2016 | Fredrickson et al. | |
| 2017/0014219 A1 | 1/2017 | Sargeant | |
| 2020/0206001 A1 | 7/2020 | Pereira et al. | |
| 2022/0354672 A1 * | 11/2022 | Pereira | A61F 2/848 |

FOREIGN PATENT DOCUMENTS

| | | |
|---|---|---|
| JP | 2004508882 A | 3/2004 |
| JP | 2005503843 A | 2/2005 |
| JP | 2007512114 A | 5/2007 |
| JP | 2007537842 A | 12/2007 |
| JP | 2011502029 A | 1/2011 |
| JP | 2011509758 A | 3/2011 |
| JP | 2011523569 A | 8/2011 |
| JP | 2014507196 A | 3/2014 |
| JP | 2014508559 A | 4/2014 |
| JP | 2014522247 A | 5/2014 |
| WO | 2000010488 A1 | 3/2000 |
| WO | 0043050 A1 | 7/2000 |
| WO | 0224112 A2 | 3/2002 |
| WO | 2005112821 A2 | 12/2005 |
| WO | 20090360014 A2 | 3/2009 |
| WO | 2009137793 A1 | 11/2009 |
| WO | 2010065026 A2 | 6/2010 |
| WO | 2010090348 A1 | 8/2010 |
| WO | 2014042875 A1 | 3/2014 |
| WO | 2014065941 A1 | 5/2014 |

OTHER PUBLICATIONS

Forer et al; "Dural Defect Repair with Fascia by a CO2 Laser System in a Porcine Model," The Laryngoscope, Lippincott, Williams & Wilkins, Inc., The American Laryngological Rhinological and Otological Society, Inc., pp. 1002-1006, Jun. 2006.

Govorov et al; "Generating Heat with Metal Nanoparticles," Nano Today, vol. 2, Issue 1, pp. 30-38, Feb. 2007.

* cited by examiner

STENT-CONTAINING MEDICAL DEVICES AND METHODS OF USING THE SAME

CROSS-REFERENCE APPLICATION

This application is a continuation of U.S. patent application Ser. No. 16/802,178, filed Feb. 26, 2020, which is a continuation of U.S. patent application Ser. No. 14/753,201, filed Jun. 29, 2015, now U.S. Pat. No. 10,610,386, which claims the benefit of priority under 35 U.S.C. § 119 to U.S. Provisional Application Ser. No. 62/018,262 filed Jun. 27, 2014, the disclosures of which are herein incorporated herein by reference in their entirety.

FIELD

The present invention relates to stent-containing medical devices and to methods of treatment using the same.

BACKGROUND

A stent is a small mesh tube that is used to treat narrowed or weak lumens (e.g., an artery, vein, bile duct, esophagus, intestine, lung, etc.), for example, to counteract lumen constriction due to various diseases and conditions. Stents can be formed from metals, polymers or other suitable material. Stents can be biostable or bioresorbable, drug eluting or non-drug-eluting. The most common use for a stent is in coronary arteries. Other common types of stents besides coronary stents include peripheral stents, ureteral stents (e.g., to ensure patency of the ureter), biliary stents (e.g., to treat obstruction in the bile or pancreatic duct), esophageal stents (e.g., to treat blockages of the esophagus), enteral stents (e.g., to treat blockage of the small bowel or colon), and airway stents (e.g., to treat blockage of the trachea or bronchi), among others.

In some cases, stents are covered. If the covering of the covered stent is porous, typically for use in the vasculature, it is often called a stent-graft. Stent-grafts are used in the treatment of abdominal aortic aneurysms and weakened peripheral arteries. Other covered stents may be used for the treatment of malignant or benign strictures of the esophagus as well leaks and/or perforations in various body lumens, among other uses. In some cases covered stents are temporarily placed and are removable.

Fixation is extremely important in the placement of a stent, whether covered, partially covered or non-covered, because if the implant migrates, the treatment can be compromised and further complications can occur.

As one specific example, placement of covered self-expanding metal or polymer stents has been the first choice for palliative therapy of unresectable esophageal cancer. These stents are also highly effective for the management of benign (peptic, postsurgical, corrosive) strictures, esophageal leaks, perforations and fistula. In most cases, rapid relief of dysphagia and adequate oral intake of nutrients can be achieved. If the stent migrates from the esophagus, such as into the stomach or small intestine causing an obstruction, the patient can suffer severe pain and fever resulting in an additional surgery to remove the stent. The same also applies for other GI and airway stents.

As another specific example, abdominal aortic aneurysm (AAA) stent-grafts are often used to address arterial aneurysms, which are characterized by a weak artery wall. Over time, blood pressure and other factors can cause this weak area to bulge like a balloon and it can eventually enlarge and rupture. The AAA stent graft is designed to seal tightly with the artery above and below the aneurysm. The graft is stronger than the weakened artery and it allows blood to pass through it without pushing on the bulge. If the stent-graft were to migrate, the seal above the aneurysm may be compromised. This may result in blood flowing into the aneurysmal sac causing it to grow and possible rupture. Re-intervention may be required.

SUMMARY

In accordance with some aspects of the present disclosure, stent-containing devices are provided which comprise an associated bonding material, wherein the stent-containing device is configured to bond to a lumen when exposed to an energy source while the stent-containing device is in contact with the lumen.

In some aspects, the present disclosure features medical devices comprising (a) a stent component, (b) an optional covering material, and (c) a bonding material associated with the stent component, the optional covering material, or both; wherein the medical device is configured to be implanted a patient and to bond to adjacent patient tissue when the bonding material is exposed to energy from an energy source.

In certain embodiments, which may be used in combination with any of the above aspects, the bonding material comprises a tissue solder material, the bonding material comprises a tissue solder and a photosensitizing dye, or the bonding material comprises a tissue solder and an energy absorber.

In certain embodiments, which may be used in combination with any of the above aspects and embodiments, the bonding material comprises a tissue solder selected from chitosan, albumin, collagen, elastin, fibrinogen, nano-peptides, derivatives of the foregoing, and combinations of two or more of the foregoing.

In certain embodiments, which may be used in combination with any of the above aspects and embodiments, the bonding material comprises a tissue solder and a photosensitizing dye selected from rose bengal dye, methylene blue dye, fluorescein dye, indocyanine green, basic fuchsin, fen, xanthane dye, riboflavin dye, lumichrome dye, flavin, lumiflavin dye, Reactive Black 5 dye, and combinations of two or more of the foregoing.

In certain embodiments, which may be used in combination with any of the above aspects and embodiments, the bonding material comprises a tissue solder and an energy absorber selected from chromophores, superparamagnetic iron oxide nanoparticles (SPIONs), gold nanorods, gold nanoshells, gold nanocages and combinations of two or more of the foregoing.

In certain embodiments, which may be used in combination with any of the above aspects and embodiments, the bonding material comprises a tissue solder and a synthetic polymer selected from polylactic acid, polyglycolic acid, poly(lactic acid-co-glycolic acid), polydioxanone, polycaprolactone, and combinations of two or more of the foregoing.

In further aspects, which may be used in combination with any of the above aspects and embodiments, the bonding material is associated with the medical device (a) by a coating of the bonding material over at least a portion of the stent component, the optional covering material, or both, (b) by integrating the bonding material into at least a portion of the stent component, the optional covering material, or both, or (c) a combination of the foregoing.

In further aspects, which may be used in combination with any of the above aspects and embodiments, the bonding material is associated with the ends of the medical device but not the center of the medical device or the bonding material is provided as a series of bands or islands along the length of the medical device.

In further aspects, which may be used in combination with any of the above aspects and embodiments, the medical device comprises the optional covering material. The covering material may, for example, cover the entire stent component or cover only a portion of the stent component. For instance, in certain embodiments, only the ends of the stent component may be covered by the covering material, or the covering material may be provided with a plurality of openings that provide areas where the stent component is not covered by the covering material. In certain embodiments, the covering material covers only a portion of the stent component, and the bonding material is associated with the stent component in areas of the stent component not covered by the covering material.

In further aspects, which may be used in combination with any of the above aspects and embodiments, the medical device comprises the optional covering material, and the covering material is sufficiently transparent to the energy from the energy source such that bonding material that is positioned abluminally relative to the covering material can be activated using an energy source positioned luminally relative to the covering material.

Other aspects of the present disclosure provide methods of attaching a stent-containing medical device to a lumen, wherein energy from an energy source is applied to a bonding material that is associated with the stent-containing medical device, such that the bonding material is activated and the stent-containing device is attached to the lumen. In certain embodiments, stent-containing medical devices, such as those described in any of the above aspects and embodiments, are employed in the method.

Yet other aspects of the present disclosure features kits that comprise any combination of any two or more of the following items: (a) a stent-containing medical device comprising a stent component, an optional covering, and an optional bonding material associated the stent component, the optional covering, or both, (b) a bonding material in solid form or in fluid form, (c) a surgical device, either with or without an associated energy source, that is configured to receive and place the medical device in a subject, (d) a guide wire, either with or without an associated energy source, or (e) a standalone energy source. In certain embodiments, stent-containing medical devices, such as those described in any of the above aspects and embodiments, are employed in the kit.

An advantage of the present disclosure is that compositions, devices, kits and procedures are provided whereby stent-containing medical devices may be implanted in body lumens, accompanied by bonding material activation, such that migration of the devices within the body lumens is minimized or prevented after implantation.

Another advantage of the present disclosure is that compositions, devices, kits and procedures are provided whereby stent-containing medical devices, particularly covered stents, may be implanted in body lumens, accompanied by bonding material activation, such that the devices are sealed with respect to the body lumens.

DETAILED DESCRIPTION

The present disclosure pertains to methods, compositions, devices and kits that are useful in the implantation and fixation of stent-containing medical devices, for example, bare stents, drug eluting stents, partially covered stents, and fully covered stents, among others, in a body lumen of a subject, typically a vertebrate subject, and more typically a mammalian subject, such as human subject, pet or livestock. The devices may be implanted and fixed in a variety of lumens, for example, in a blood vessel (e.g., artery, vein etc.), a lumen of the gastrointestinal tract (e.g., esophagus, stomach, duodenum, small intestine, large intestine, colon, biliary duct, etc.), a urogynecological lumen (e.g., ureter, urethra, fallopian tube, etc.), or an airway lumen (e.g. trachea, bronchi, etc.), among other lumens, for instance, to prevent migration within the lumen and/or create a seal with the lumen (e.g., in the case of a covered stent). In various embodiments, stent-containing devices are used to provide one or more of the following functions: support the patency of the body lumen, strengthen the body lumen wall, seal the body lumen wall, and prevent tissue ingrowth into the body lumen, among other functions.

According to one aspect, the present disclosure is directed to stent-containing devices that are configured for implantation in a body lumen which comprise (a) a stent component, (b) an optional covering material and (c) a bonding material. The bonding material is associated with at least a portion of the stent-containing device (e.g., associated with the stent component, the optional covering, or both), such that the stent-containing devices are capable of bonding to adjacent patient tissue when exposed to an energy. For example, the bonding material may be associated with the device by one or more of the following strategies, among others: (a) the bonding material may be coated onto all or a portion of the stent component, (b) the bonding material may be integrated into all or a portion of the stent component, (c) the bonding material may be coated onto all or a portion of the optional covering material or (d) the bonding material may be integrated into all or a portion of the optional covering material.

The stent-containing device is introduced into a body lumen, for example, a blood vessel, a lumen of the gastrointestinal tract, a urogynecological lumen, or an airway lumen, among others, using a suitable procedure. Energy is then applied to the bonding material such that that bonding material is activated and the stent-containing device is attached to the body lumen tissue.

Different energy sources may be used for device attachment, depending on the mechanism for tissue bonding that is employed. The energy source may be, for example, a source of heat or light, such as a laser or a light-emitting diode (LED). Infrared and near-infrared laser sources include carbon dioxide ($CO_2$), thulium-holmium-chromium, holmium, thulium, and neodymium rare-earth-doped-garnets (THC:YAG, Ho:YAG, Tm:YAG, and Nd:YAG, respectively), and gallium aluminum arsenide diode (GaAlAs) lasers, among others. Visible sources include potassium-titanyl phosphate (KTP) frequency-doubled Nd:YAG, and argon lasers, among others. Other energy sources include radiofrequency sources (e.g., a microwave source), radiation sources (e.g., x-ray radiation, gamma radiation, etc.), or a locally produced plasma. Argon plasmas are currently employed in various medical applications, including argon beam coagulators, which ionize argon gas to form an argon plasma and then use the plasma to deliver thermal energy to nearby tissue. In the present disclosure, an argon beam may be used as a source of heat for tissue bonding.

In certain embodiments, the energy source is provided in a stand-alone unit. In other embodiments, the energy source is combined with another device. For example, the energy source may be combined with a delivery device, such as a guide wire or catheter.

In some embodiments, the energy source is connected to a control unit, which controls the energy emitting from the energy source. Preferably, the amount of energy is sufficient to activate the bonding material without significantly damaging the underlying tissue. In some embodiments, the control unit is designed to accept user input (e.g., via physical buttons, touchscreen, etc.), thereby allowing treatment parameters to be set by a health care provider.

In some embodiments, the energy source is controlled without the use of a sensor (e.g., based on the experience of the surgeon or based on a suitable energy output algorithm). In other embodiments, a sensor is used in conjunction with the energy source to provide feedback regarding the amount of energy being directed to the bonding site, and this feedback can be used to adjust the energy source output. For example, in certain embodiments, the sensor is a temperature sensor which detects the amount of heat at the bonding site. In these embodiments, suitable software can be employed to adjust the output of the energy source based on input from the temperature sensor. The sensor may be provided, for example, in the same device as the energy source or in a device that is different from the device containing the energy source. The sensor may be provided, for example, in a medical device that is used for device delivery (either with or without the energy source).

A variety of bonding materials can be used in conjunction with the present disclosure.

In this regard, laser tissue soldering processes are known in the surgical art whereby tissue is bonded by applying a solder (commonly, a biological polymer) to the tissue, after which a laser is used to activate the solder and form a bond. Without wishing to be bound by theory, it has been reported that the mechanism of laser tissue soldering appears to include a heating-induced protein denaturation-renaturation process. See, e.g., B. Forer et al., *Laryngoscope* 116: June 2006, 1002-1006.

Solder materials are used in the present disclosure as bonding materials to bond stent-containing device materials to tissue, for example, by the application of heat to a solder material while it is in contact with a stent-containing device material (e.g. a stent component material or an optional covering material) and tissue, such that the stent-containing device material is bonded to the tissue. As indicated above, beneficial energy sources for the application of heat include light sources (e.g., lasers, etc.), radiofrequency sources (e.g., microwave sources, etc.) and plasma sources (e.g., argon beams, etc.), among others.

Particularly beneficial solder materials have a relatively low activation temperature and are bioresorbable. For example, the solder may be bioresorbed over time, typically between about 4 days and six months (e.g., ranging from 4 days to 1 week to 2 weeks to 1 month to 2 months to 3 months to 6 months) (i.e., ranging between any two of the preceding numerical values), depending on the solder that is used. The bioresorption rate may be adjustable to provide bioresorption within this range, or to sooner than or after this range, by adjusting the chemistry of the solder.

Specific solder materials for use in conjunction with the present disclosure include solders of biological origin and synthetic solders. Examples of solders of biological origin include those based on biological polymers, for example, polypeptides including nano-peptides and proteins such as albumin, collagen, elastin, fibrin, fibrinogen, thrombin, prothrombin protein derivatives, as well as polysaccharides including chitosan, among others. In some embodiments, two, three, four or more solder materials such as those described above are employed. Specific examples include a combination of albumin and collagen, a combination of albumin and chitosan, a combination of collagen and chitosan, and a combination of albumin, collagen, and chitosan, among many other possible combinations.

Other polymers that may be added include: water soluble or bioresorbable polymers, for example, synthetic water soluble or bioresorbable polymers, such as polylactic acid, polyglycolic acid, polydioxanone, polycaprolactone, tyrosine based polyesters, tyrosine based polycarbonates, polyesteramides, polyanhydrides, polyhydroxyalkanoates, polyethylene glycols, polyorthoesters, pluronics, such as block copolymers of ethylene glycol and propylene glycol, polyamides, polyvinylalcohol, hydroxyl substituted poly(meth)acrylates, polyethylene glycol substituted (meth)acrylates, (methacrylate-b-polyethers) or copolymers derived from these monomers, among others. One or more of these water soluble or bioresorbable polymers may be mixed with solders of biological origin, such as those above, to change the properties of the solder material. As a specific example, PLGA can be mixed with albumin to increase the flexibility of the albumin solder.

In some embodiments, at least one energy absorber is used within the solder material to enhance heating efficiency and/or heat distribution within the solder material. Energy absorbers include chromophores, for example, light-specific dyes such as indocyanine green (ICG), fluorescein, basic fuchsin, and fen, nano-metals such as nano-gold (e.g., gold nanorods, gold nanoshells, gold nanocages, etc.) and SPIONs (superparamagnetic iron oxide nanoparticles), among other materials. Specific examples include ICG-doped albumin, fluorescein-dye-doped albumin, and nano-gold-doped albumin, among many others. Metal (e.g., gold, etc.) or semiconductor nanoparticles, including rods, nanoshells, and other shapes, may be included in the solder material and heated by excitation at their plasmon frequencies. For further information, see, e.g., Alexander O. Govorov et al, "Generating heat with metal nanoparticles," *Nano Today*, Volume 2, Issue 1, February 2007, Pages 30-38.

Photochemical tissue bonding processes are known the surgical art. These processes take advantage of the photochemical reactions that occur at intimately associated tissue surfaces, which are stained with a photosensitizing dye (e.g., dyed tissue surfaces which are placed in contact with one another). Without wishing to be bound by theory, it is believed that the dye absorbs photons of visible radiation and promotes the formation of covalent bonds between molecules on the approximated tissue surfaces. For example, reactive species that are produced upon light activation of the dye can react with potential electron donors and acceptors such as amino acids in proteins (e.g., tryptophan, tyrosine, cysteine, and so forth). In this regard, photochemical methods have been reported to form crosslinks in collagen type I molecules. See, Barbara P. Chan et al., *Journal of Surgical Research* 108, 77-84 (2002).

In certain aspects of the present disclosure, photosensitizing dyes are used to bond stent-containing devices to tissue surfaces, for example, by the application of light of a suitable wavelength to a photosensitizing dye and a solder material (e.g., a biological solder material, including those set forth above, among others) in intimate association with a stent-containing device and a tissue surface (e.g., a photosensitizing dye admixed with a solder material or coated on a surface of a solder material that is in contact with and disposed between a stent-containing device and tissue), such that the stent-containing device is bonded to the tissue. A light-emitting energy source such as a low-power laser or light-emitting diode (LED) may be used for this purpose, among others.

Specific examples of photosensitizing dyes include xanthene dyes such as rose bengal, methylene blue and fluorescein, riboflavin dye (e.g., riboflavin-5-phosphate), lumichrome dye, lumiflavin dye, Reactive Black 5, thiazine dye, naphthalimides (e.g., 1,8-naphthalimide), erythrosine, N-hydroxypyridine-2-(1H)-thione (N-HTP), protoporphyrin I through protoporphyrin IX, coproporphyrins, uroporphyrins, mesoporphyrins, hematoporphyrins and sapphyrins, chlorophylis, e.g., bacteriochlorophyll A, Photofrin®, synthetic diporphyrins and dichlorins, phthalocyanines with or without metal substituents, chloroaluminum phthalocyanine with or without varying substituents, O-substituted tetraphenyl porphyrins, 3,1-meso tetrakis (o-propionamido phenyl) porphyrin, verdins, purpurins, tin and zinc derivatives of octaethylpurpurin, etiopurpurin, hydroporphyrins, bacteriochlorins of the tetra(hydroxyphenyl) porphyrin series (e.g., protoporphyrin I through protoporphyrin IX, coproporphyrins, uroporphyrins, mesoporphyrins, hematoporphyrins and sapphyrins), chlorins, chlorin e6, mono-1-aspartyl derivative of chlorin e6, di-1-aspartyl derivative of chlorin e6, tin(IV) chlorin e6, meta-tetrahydroxphenylchlorin, benzoporphyrin derivatives, benzoporphyrin monoacid derivatives, tetracyanoethylene adducts of benzoporphyrin, dimethyl acetylenedicarboxylate adducts of benzoporphyrin, Diels-Adler adducts, monoacid ring "a" derivative of benzoporphyrin, sulfonated aluminum PC, sulfonated AlPc, disulfonated, tetrasulfonated derivative, sulfonated aluminum naphthalocyanines, naphthalocyanines with or without metal substituents and with or without varying substituents, chlorophylis, bacteriochlorophyll A, anthracenediones, anthrapyrazoles, amino anthraquinone, phenoxazine dyes, phenothiazine derivatives, chalcogenapyrylium dyes, cationic selena and tellurapyrylium derivatives, ring-substituted cationic PC, pheophorbide derivative, naturally occurring porphyrins, hematoporphyrin, ALA-induced protoporphyrin IX, endogenous metabolic precursors, 5-aminolevulinic acid, benzonaphthoporphyrazines, cationic imminium salts, tetracyclines, lutetium texaphyrin, texaphyrin, tin-etio-purpurin, porphycenes, benzophenothiazinium, eosin, erythrosin, cyanines, merocyanine 540, selenium substitued cyanines, flavins, riboflavin, proflavin, quinones, anthraquinones, benzoquinones, naphthaldiimides, victoria blue, toluidine blue, dianthroquinones (e.g., hypericin), fullerenes, rhodamines and photosensitive derivatives thereof.

An advantage of using light rather than heat is that there is less risk of causing damage to the tissue (cell death) from heat. Another advantage of using light, rather than heat, to achieve device-to-tissue bonding is that complications due to uneven heat distribution can be reduced or eliminated.

In addition, the use of wavelength-specific absorbers such as chromophores enables differential absorption between the chromophore-containing regions and surrounding tissue. One advantage is a selective absorption of radiation by the target, without the need for a precise focusing. Moreover, lower power levels may be used because of the increased absorption of chromophore-containing regions, leading to reduced tissue damage.

Stent-containing devices include self-expanding and balloon-expandable devices. The stent component of the stent-containing device may be metallic or polymeric, biostable or biodegradable. In certain embodiments, the stent component is formed from a metal selected from stainless steel, nitinol, titanium and Elgiloy (an alloy comprising cobalt, chromium and nickel), among others. In certain other embodiments, the stent portion is formed from a biodegradable polymer selected from polylactide, polyglycolide, poly(lactide-co-glycolide), polycaprolactone, and polydioxanone, among others. In certain additional embodiments, the stent portion is formed from a biodegradable metal such as iron, iron alloy, magnesium and magnesium alloy, among others.

The stent struts can be coated with a coating material that does not span the cells between the struts (coated stent). The stent struts can be covered by a covering material that spans the cells between the stent struts (covered stent).

As previously indicated, stent-containing device materials for use in accordance with the present disclosure include bare stents, drug eluting stents (which may have a drug eluting coating), and stents that are partially or completely covered by a covering material. Covering materials include non-porous covering materials (e.g., solid films) and porous covering materials, including porous films (e.g., expanded polytetrafluoroethylene, or ePTFE) and fiber based coverings. In this regard, stent coverings for use in the present disclosure may be formed using a variety of fiber-based construction techniques and include, for example, woven stent coverings and non-woven stent coverings (e.g., knitted, braided, coiled, randomly wrapped, spunbound, etc.).

Covering materials may be selected from various synthetic and natural polymers. Beneficial polymers for forming coverings for stent-containing devices may be selected from the following, among others: (a) polysiloxanes (i.e., silicones), including polydimethylsiloxane (PDMS), among others, (b) fluoropolymers, including homopolymers and copolymers of C2-C8 alkenes in which one or more hydrogen atoms are substituted with fluorine, for example, polytetrafluoroethylene (PTFE), polyvinylidene fluoride (PVDF), poly(vinylidene fluoride-co-hexafluoropropene) (PVDF-HFP), among others, (c) polyamides such as nylons, among others, (d) polyesters, including, for example, polyethylene terephthalate, among others, (e) polyurethanes such as polyether-based polyurethanes, polycarbonate-based polyurethanes, and polyalkene-based polyurethanes (e.g., polyisobutylene-based polyurethanes), among others, (f) polyolefin homopolymers and copolymers, including homopolymers and copolymers of C2-C8 alkenes, for example, polyethylene and polypropylene, among others, (g) polyoxyalkylenes including homopolymers of trioxane (e.g., polytrioxane, also known as polyoxymethylene or acetal) and copolymers of trioxane (e.g., copolymers of trioxane and dioxane), and (h) styrenic copolymers such as alkene-styrene copolymers, including block copolymers comprising one or more polystyrene blocks and one or more polyalkene blocks, for instance, poly(styrene-b-isobutylene-b-styrene) (SIBS) or poly(styrene-b-ethylene/butylene-b-styrene) (SEBS), among others.

The fiber width (e.g., the diameter of a circular fiber) in a fiber-based stent coverings may vary widely. In certain embodiments, the stent-containing devices of the present disclosure may have fiber widths ranging from 1 μm to 500 μm (for example, ranging from 1 μm to 2.5 μm to 5 μm to 10 μm to 25 μm to 50 μm to 100 μm to 250 μm to 500 μm) (i.e., ranging between any two of the preceding numerical values), among other values. In certain embodiments, fibers may be provided with surface features, for example, to increase the surface area of the fibers and thus the contact area between the fibers and a bonding material coating.

Porous stent coverings in accordance with the present disclosure may also have a wide range of pore sizes. In various embodiments, the stent-containing devices of the present disclosure may have area pore sizes ranging from 1 μm to 100 μm (for example, ranging from 1 μm to 2.5 μm to 5 μm to 10 μm to 25 μm to 50 μm to 100 μm) (i.e., ranging between any two of the preceding numerical values).

Bonding material may be associated with a stent-containing device in various ways. For example, bonding material may be applied as a coating on all or a portion of a bare stent component, applied as a coating on all or a portion of a coated stent (e.g., a drug-eluting stent), or applied as a coating on all or a portion of a partially or fully covered stent. As another example, bonding material may be admixed with impregnated into all or a portion of a stent component material (particularly a polymeric stent material), admixed with impregnated into all or a portion of a stent coating material, admixed with impregnated into all or a portion of a stent covering material, or a combination of the foregoing. As another example, a layer (e.g., a sheet) of bonding material may be laminated onto all or a portion of a stent component material, laminated onto all or a portion of a stent coating material, laminated onto all or a portion of a stent covering material, or a combination of the foregoing. A stent covering material may be coated, impregnated, and/or laminated with a bonding material either before or after the stent covering material is associated with the stent component.

The bonding material may be present, for example, over the entire length of the stent-containing device or only at certain points along the length of the stent-containing device, for instance, associated with the ends of the stent-containing device. This allows potions of the stent-containing device to be largely free of bonding material, which reduces bonding material consumption, among other advantages.

Bonding material may be impregnated into and/or coated onto another material using various techniques which may be selected, for example, from dipping techniques, spraying techniques, spin coating techniques, web coating techniques, electrostatic techniques, techniques in which bonding material is selectively applied to certain regions of the stent-containing device but not others, for example, through the use of a suitable application device such as a sprayer, brush, roller, pen, or printer (e.g., screen printing device, ink jet printer, etc.).

If the bonding material does not adhere to the stent, the (optional) covering material, or both, an intermediate layer that bonds to (a) the bonding material and (b) the stent, the (optional) covering material, or both, may be used, for example, as a tie layer. In certain embodiments, the intermediate layer may be transparent to the energy that is applied to the bonding material.

As previously indicated, various embodiments of the present disclosure pertain to stent-containing devices in which the stent component may be, for example, metallic or polymeric, biostable or bioresorbable, self-expanding or balloon expandable.

In some embodiments, a stent component may be formed entirely of bonding material.

In some embodiments, a stent component is partially or fully coated or impregnated with bonding material.

In some embodiments, the bonding material may be bioresorbable, for example, leaving nothing but the stent component and/or optional covering material behind after integration (e.g., where the stent or optional covering material is biostable or bioresorbable). As noted above, the rate of bioresorption may be adjusted, for example, from days to weeks to months.

Figure 1:
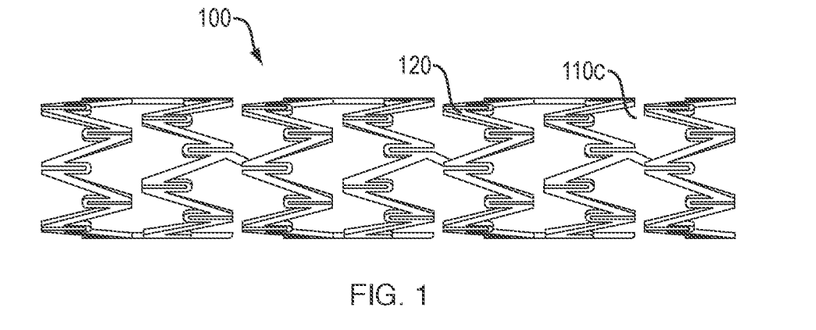
FIG. 1 is a schematic illustration of a solder-containing stent, in accordance with an embodiment of the present disclosure.

In some embodiments, the stent component elements (e.g., stent wire, stent struts, etc.) can be coated in bonding material, leaving the cells open. One specific embodiment is shown in FIG. 1, which shows a stent 100, whose structural elements are completely coated with a bonding material 120, but in which the stent cells 110c are left open.

Figure 2:
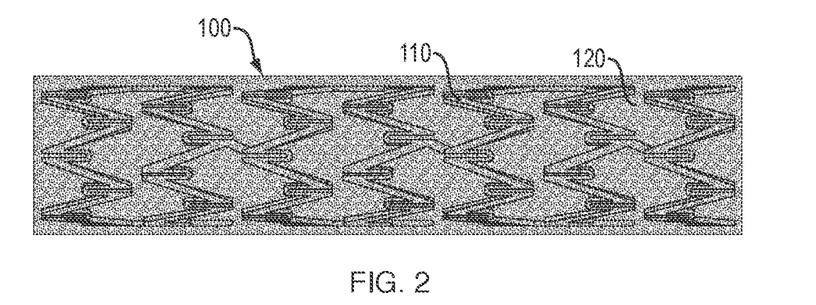
FIG. 2 is a schematic illustration of a solder-containing stent, in accordance with another embodiment of the present disclosure.

In other embodiments, the bonding material may cover the stent cells. A specific embodiment is shown in FIG. 2, which is a schematic illustration of a stent 100, whose stent cells are covered with bonding material 120. The bonding material may be, for example, only on the outer (abluminal) surface of the structural elements 110, only on the inner (luminal) surface of the structural elements 110, or may completely enclose the structural elements 110.

Figure 3:
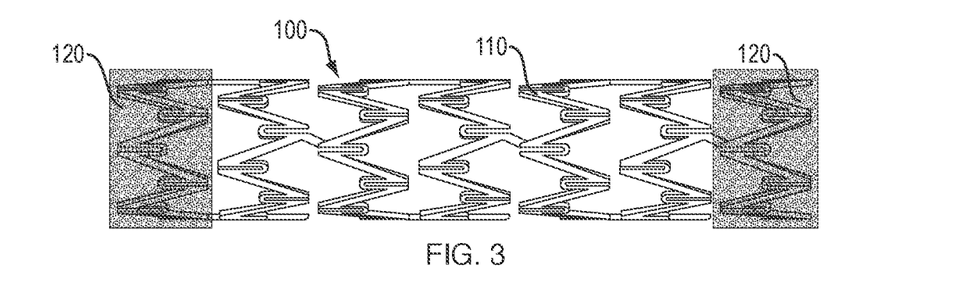
FIG. 3 is a schematic illustration of a solder-containing stents in accordance with another embodiment of the present disclosure.
Figure 4:
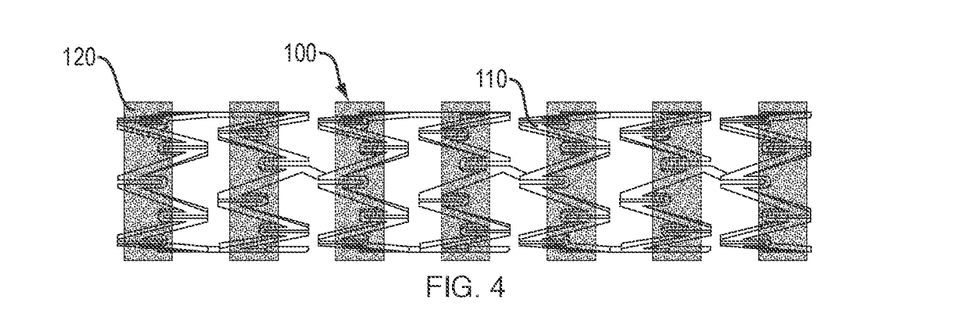
FIG. 4 is a schematic illustration of a solder-containing stent, in accordance with another embodiment of the present disclosure.

In some embodiments, the stent is partially coated or impregnated with bonding material. A specific embodiment is schematically shown in FIG. 3, which shows a stent 100, wherein the bonding material 120 is applied to structural elements 110 only at the ends of the stent. Another specific embodiment is schematically shown in FIG. 4, wherein the bonding material 120 is applied to structural elements 110 at intervals along the length of the stent 100. In the embodiments shown in FIGS. 3 and 4, bonding material 120 spans at least portions of the stent cells. The bonding material 120 may be, for example, only on the outer (abluminal) surface of the structural elements 110, only on the inner (luminal)

surface of the structural elements 110, or may completely enclose the structural elements 110. In other embodiments, the structural elements are coated with bonding material, leaving the stent cells open.

In some embodiments, stent-containing devices are provided wherein a stent component is partially or fully covered with a covering material. As elsewhere, the stent component may be metallic or polymeric, bio stable or bioresorbable, self-expanding or balloon expandable. The covering material may be biostable or bioresorbable, porous or nonporous. The covering material may be a woven or nonwoven fibrous construct. The covering material may fully or partially cover the stent component.

A partially or fully covered stent may, in turn, be partially or fully coated with a bonding material. For example, a partially or fully covered stent may be coated with a bonding material on the outside (abluminal) surface, but not the inside (luminal) surface. A partially or fully covered stent may be coated with bonding material at or near the ends of the stent, or in any other strategic areas. A partially or fully covered stent may be coated with bonding material on the covering but not on the stent component.

Figure 5A:
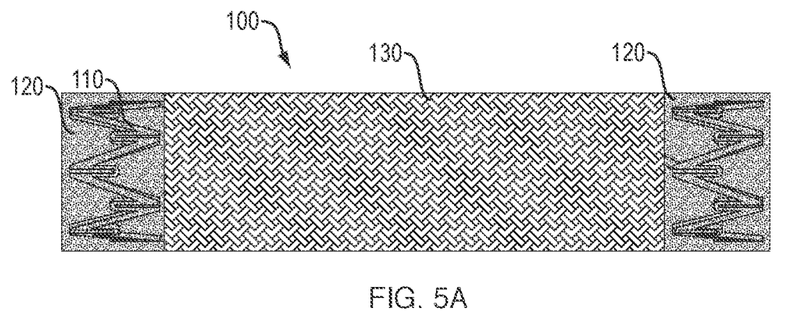
FIG. 5A is a schematic illustration of a solder-containing stent, in accordance with another embodiment of the present disclosure.

A specific embodiment is schematically shown in FIG. 5A, wherein only the central area of the stent portion is covered in a covering material 130. Bonding material 120 is applied to structural elements 110 at the ends of the stent in the areas that are not covered in the covering material 130. In the embodiment shown, bonding material 120 spans the stent cells, in which case the bonding material 120 may be present, for example, only on the outer (abluminal) surface of the structural elements 110, only on the inner (luminal) surface of the structural elements 110, or may completely enclose the structural elements 110. In other embodiments, the structural elements are coated with bonding material, leaving the stent cells open.

Figure 5B:
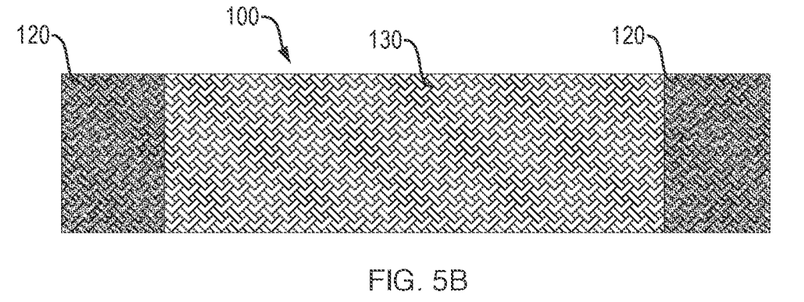
FIG. 5B is a schematic illustration of a solder-containing stent, in accordance with another embodiment of the present disclosure.

Another specific embodiment is schematically shown in FIG. 5B, wherein the entire stent is covered in a covering material 130 and bonding material 120 is applied to the covering material at the ends of the stent. In certain embodiments, the covering material may be made of a material that is transparent to the bonding energy that is applied, such that bonding energy from an energy source positioned luminally relative to the covering material (i.e., inside the stent) can reach bonding material on the outer (abluminal) surface of the covering material. If an intermediate layer (not shown) is disposed between the bonding material 120 and the covering material 130, the intermediate material may be made of a material that is transparent to the bonding energy that is applied as well.

Figure 6:
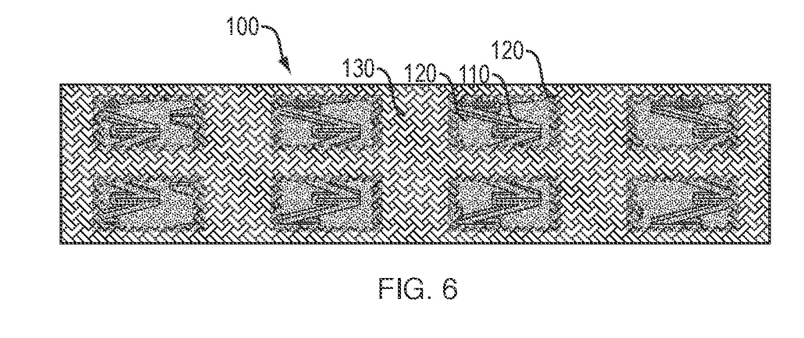
FIG. 6 is a schematic illustration of a solder-containing stent, in accordance with another embodiment of the present disclosure.

In certain embodiments, for example, as shown in FIG. 6, the covering material 130 may be have openings of varying size to allow the energy to pass through covering and activate the bonding material 120. The bonding material 120 may span the holes as shown, and may also be applied to all or a portion of the covering material 130 in some embodiments. In some embodiments, the structural elements 110 are coated with bonding material, but the stent cells are left open.

In some embodiments, bonding material is applied to the site independently of the stent-containing device, in which case the stent-containing device either may be associated with bonding material at the time of delivery (see, e.g., FIGS. 1-6) or may be free of bonding material at the time of delivery. In these embodiments, the bonding material may be applied to tissue followed by delivery of the stent-containing device, or the stent-containing device may be delivered followed by application of the bonding material.

After introduction of the device and bonding material, the device and bonding material are irradiated using a suitable energy source.

The independently applied bonding material may be applied in solid form, fluid form or a combination thereof. Where independently deposited in solid form, the bonding material may be, for example, in the form of a patch or in a film or tape mounted onto a device suitable for radial expansion (e.g., a balloon) that can be pressed against a lumen wall by expanding the device (e.g., by inflating the balloon). Where independently deposited the form of a fluid, the bonding material may be, for example, in the form of a liquid, paste or gel (e.g., an organic or aqueous liquid, paste or gel comprising a solider material and/or photosensitizing dye), which is deposited using a suitable device such as a catheter. For example, the bonding material may be applied via a catheter to a body lumen prior to deployment of the stent-containing device or the bonding material may be deposited onto the stent-containing device after deployment via a catheter. The bonding material and stent-containing device are then irradiated via a suitable energy source, for example, using an energy source integrated into the depositing catheter or another means.

In certain embodiments, bonding material may be applied to a body lumen without implanting a stent-containing device. Where deposited in the solid form, the bonding material may be, for example, in the form of a patch or in a film or tape mounted onto a device suitable for radial expansion. Once pressed against the lumen wall, the bonding material may then be welded to the wall by exposing it to energy. This may be used, for example, to repair and/or seal tears in the lumen. In other embodiments, a bonding material in fluid form may be used to repair and/or seal tears in the lumen.

As previously noted, a variety of energy sources may be employed in the present disclosure. In some embodiments, the energy source is provided in conjunction with its own independent device, whereas in other embodiments, the energy source may integrated into a delivery device. In various embodiments, the energy source is adapted to radially direct energy outward from the side of the device. In certain cases, the energy source is rotatable (e.g., manually or mechanically), allowing energy to be directed in a full circle (i.e., 360° irradiation). Full circle irradiation may be also achieved, for example, by directing energy from around the entire circumference of the device (e.g., by means of multiple LED's, multiple optical fibers, etc.). In certain embodiments, energy is directed from the energy source through a transparent material, for example, a transparent hollow catheter shaft or a transparent balloon, among other possibilities.

Figure 10:
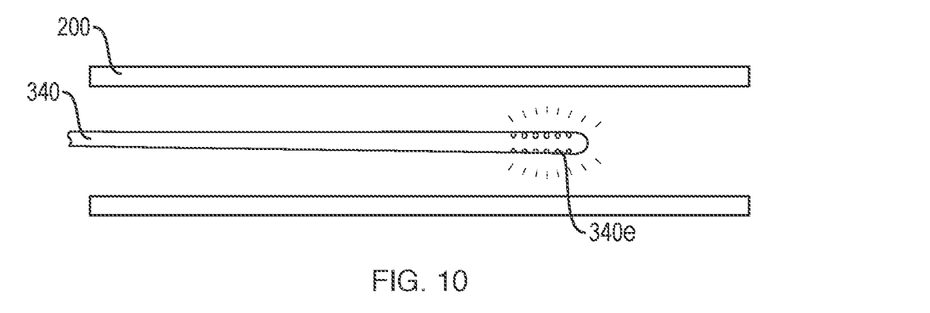
FIG. 10 is a schematic illustration of an energy-emitting device, in accordance with an embodiment of the present disclosure.

In embodiments where the energy source is provided in conjunction with its own independent device, the energy source may be, for example, integrated into an over-the-wire or monorail catheter, or the energy source may also be inserted, for example, through a lumen in a delivery catheter. In one embodiment, illustrated in FIG. 10, a light emitting device 340 may be provided with multiple light emitting elements 340e, for example, multiple LEDs or fiber optic termini, which radiate outwardly from the device.

Figure 11:
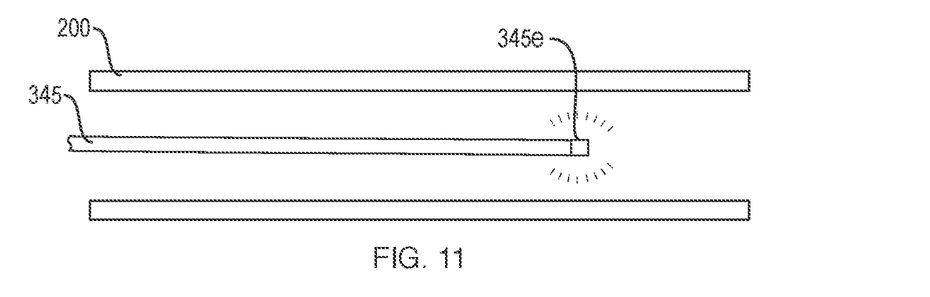
FIG. 11 is a schematic illustration of an energy-emitting device, in accordance with another embodiment of the present disclosure.
Figure 12:
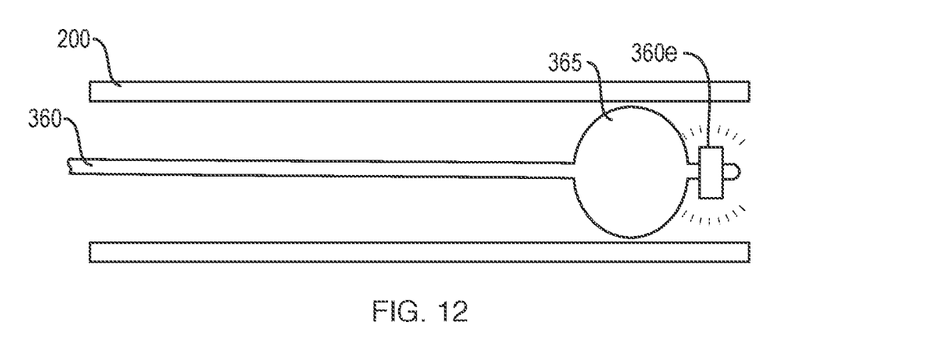
FIG. 12 is a schematic illustration of an energy-emitting device, in accordance with another embodiment of the present disclosure.

As an example of an embodiment where the energy source is integrated into a delivery device, the energy source may be integrated into a guide wire 345 as shown in FIG. 11, for instance, by using providing a guide wire with a light emitting fiber optic core 345e. Light from the core may be radially dispersed at the point where the light emerges from the core using a suitable optical element. In certain other embodiments, the energy course is integrated into a delivery catheter. For example, the delivery catheter may be provided with multiple LEDs or fiber optic termini which radiate outwardly from the delivery catheter. In some embodiments, an energy source is provided in conjunction with a balloon catheter, in which case an energy source 360e may be mounted distal to the balloon 365 of the balloon catheter 360 as shown in FIG. 12. The energy source may also be positioned proximal to the balloon or within the balloon. If positioned within the balloon, the balloon is made from a material that is transparent to the energy being irradiated. An advantage in providing the energy source within a balloon, is that the balloon helps to keep the energy source centered in the body lumen. Of course, mechanisms other than a balloon can be used to center the energy source, such as a delivery sheath or a stent.

Figure 7A:
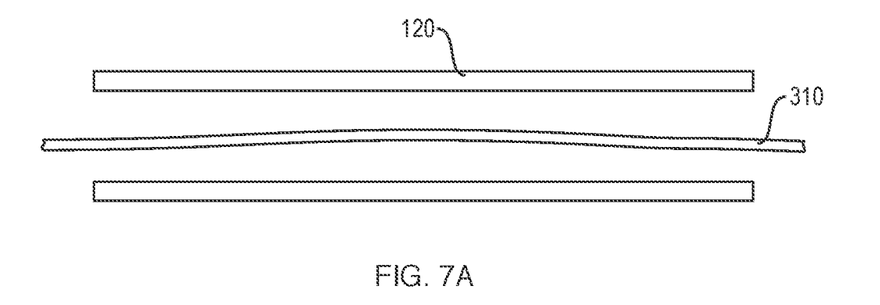
FIGS. 7A, 7B and 7C are schematic illustrations of a method of implanting a stent, in accordance with an embodiment of the present disclosure.
Figure 7B:
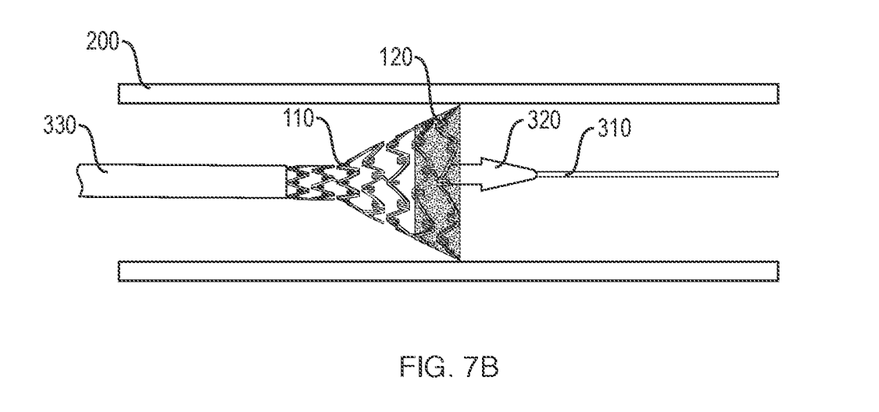
Figure 7C:
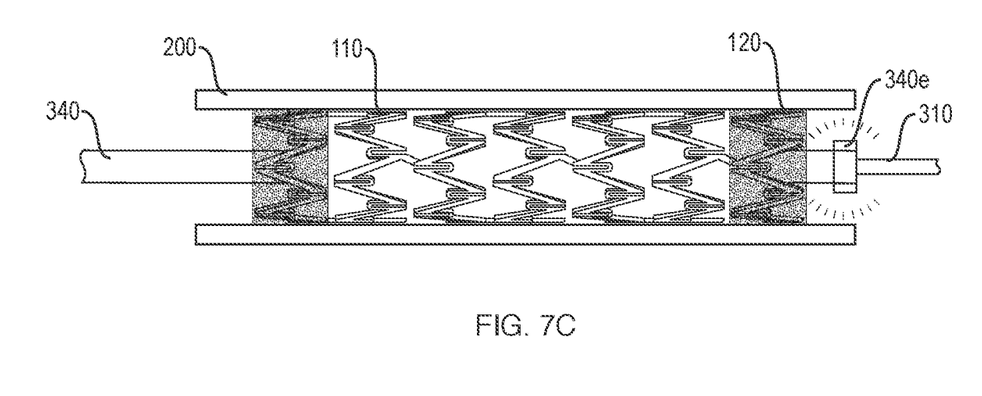

An embodiment of a procedure for delivering a stent in accordance with the present disclosure will now be described in conjunction with FIGS. 7A-7C. Initially, a guide wire 310 is positioned in a body lumen 200 as shown in FIG. 7A. Then a stent is delivered over the guide wire 310. For example, a stent may be delivered using a delivery device as known in the stent delivery art, for example, a device in which the stent is positioned between an outer catheter sheath 330 and an inner catheter member 320 and delivered to a delivery site whereupon the sheath 330 retracted, leading to self-expansion of the stent as shown in FIG. 7B. Unlike other known procedures, however, the stent in the present embodiment is one in which the stent elements 110 are coated with a bonding material 120 at the ends of the stent. In the embodiment shown, after the stent is delivered, the delivery catheter is withdrawn and a device 340 with an energy emitting element 340e is introduced over the guide wire 310, allowing the bonding material 120 to be activated and the stent to be fixed to the tissue of the body lumen 200. In other embodiments, an energy source may be included in the delivery catheter.

Figure 8A:
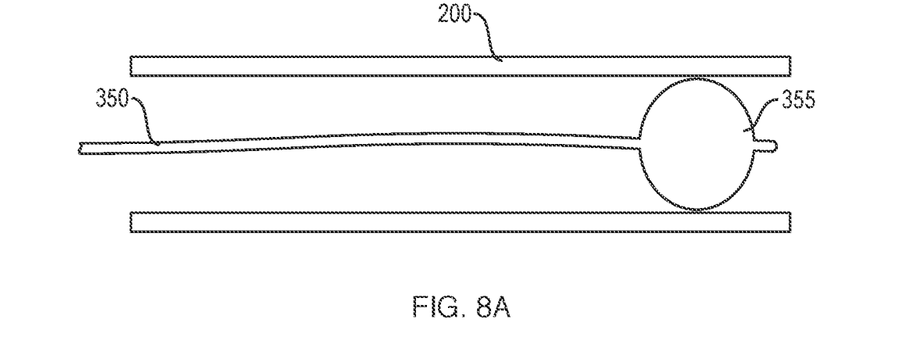
FIGS. 8A, 8B and 8C are schematic illustrations of a method of implanting a stent, in accordance with another embodiment of the present disclosure.
Figure 8B:
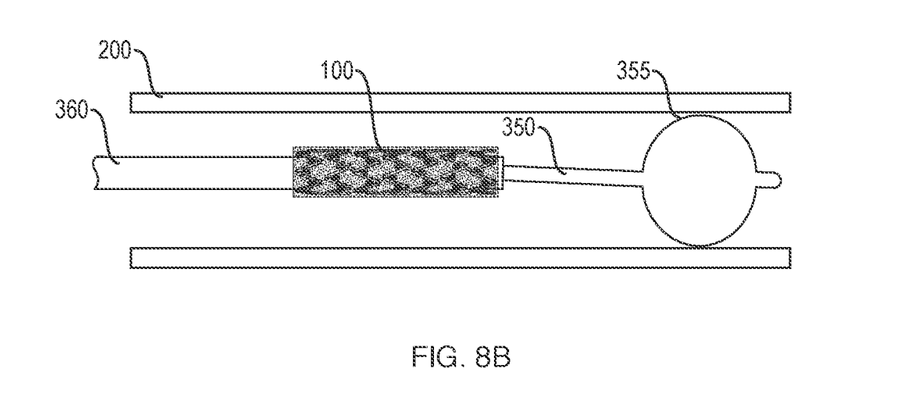
Figure 8C:
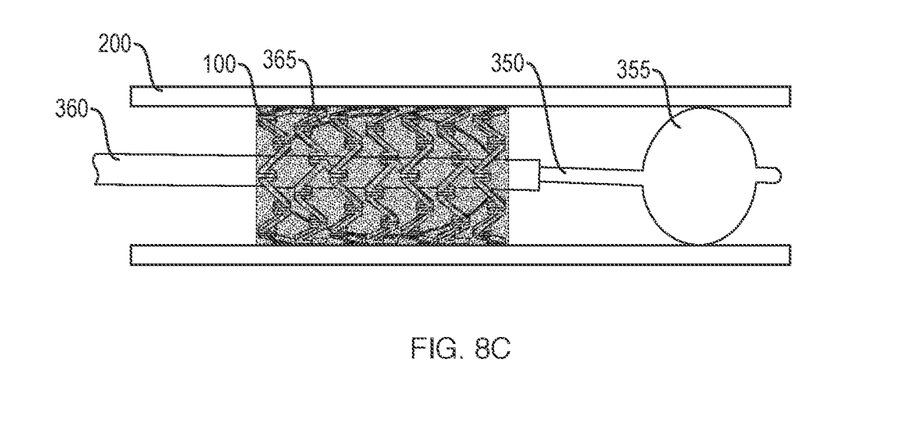

Another embodiment of a procedure for delivering a stent in accordance with the present disclosure will now be described in conjunction with FIGS. 8A-8C. In this embodiment, a first catheter 350 having a first balloon 355 is positioned in a body lumen 200 as shown in FIG. 8A, blocking flow within the body lumen 200, which may be, for example, a blood vessel. Then a stent 100 is delivered to the site, loaded on a second catheter 360 that is advanced over the first catheter 350 as shown in FIG. 8B. In the embodiment shown, the entire length of the stent 100 is provided with bonding material. As seen in FIG. 8C, the second catheter 360 has a second balloon 365 which expands the stent 100 in the body lumen 200 upon inflation. After stent expansion, an energy source within the balloon 365 of the second catheter 360 may be used to activate the bonding material in the stent 100, allowing the stent to be fixed to tissue of the body lumen 200. In other embodiments, the energy source is introduced via a separate device.

Figure 9:
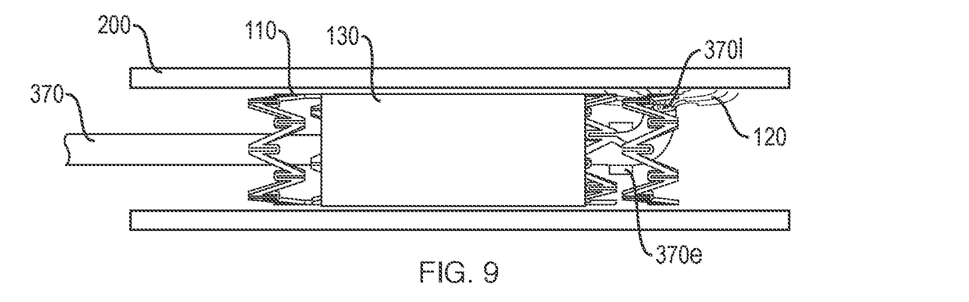
FIG. 9 is a schematic illustration of a method of implanting a stent, in accordance with yet another embodiment of the present disclosure.

Yet another embodiment of a procedure for delivering a stent in accordance with the present disclosure will now be described in conjunction with FIG. 9. In this embodiment a self-expanding or balloon expandable stent having stent elements 110 and a stent covering 130 is delivered to a body lumen 200 using a suitable delivery technique (e.g., via a catheter with a retractable sheath, a balloon catheter, etc.). Subsequently, a catheter 370 is used to deliver bonding material to the stent. For example, as shown in FIG. 9, bonding material 120 may be delivered in liquid form from one or more lumens 370l in the delivery catheter 370. After application of the bonding material 120, the stent and tissue are illuminated via a suitable energy source 370e, which is supplied on the catheter 370 in this embodiment, thereby activating the bonding material 120 such that the stent is bonded to the tissue of the body lumen 200. In other embodiments, the energy source is inserted via a separate device.

In certain embodiments, the stent-containing devices of the present disclosure may comprise various additional agents, including therapeutic agents and imaging agents, among other possible agents. Such agents may be included, for example, in a coating on or incorporated into all or a portion of the stent component material, in a coating on or incorporated into all or a portion of the bonding material and/or as a coating on or incorporated into all or a portion of the optional covering material.

"Therapeutic agents," drugs," "bioactive agents" "pharmaceuticals," "pharmaceutically active agents" and other related terms may be used interchangeably herein. Therapeutic agents include anti-restenosis, anti-hyperplasic and anti-granulation tissue agents. Therapeutic agents may be used singly or in combination.

Additional agents for use in conjunction with the stent-containing devices of the present disclosure also include imaging agents including (a) contrast agents for use in connection with x-ray fluoroscopy, including metals, metal salts and oxides (particularly bismuth salts and oxides), and iodinated compounds, among others, (b) contrast agents for use in conjunction with ultrasound imaging, including organic and inorganic echogenic particles (i.e., particles that result in an increase in the reflected ultrasonic energy) or organic and inorganic echo lucent particles (i.e., particles that result in a decrease in the reflected ultrasonic energy), and (c) contrast agents for use in conjunction with magnetic resonance imaging (MRI), including contrast agents that contain elements with relatively large magnetic moment such as God(III), MN(II), Fe(III) and compounds (including chelates) containing the same, such as gadolinium ion chelated with diethylenetriaminepentaacetic acid.

In various embodiments, the stent-containing devices may contain from less than 1 wt % to 50 wt % or more of one or more of the preceding additional agents.

In another aspect of the disclosure, medical kits useful in stent-containing device procedures are provided. The medical kits may include all or a subset of all the components useful for performing the procedures. For example, the medical kits may comprise any combination of any two, three, four, or more of the following items: (a) a stent-containing device, either without or with an associated bonding material, (b) a bonding material, for example, in fluid form or solid form, (c) one or more medical devices (e.g., a guide wire, a stent delivery device, and/or a device that is used to apply bonding material), (d) an energy source (e.g., in a stand-along unit or associated with a surgical instrument), (e) suitable packaging material, and (f) printed material with one or more of the following: (i) storage information and (ii) instructions regarding how to implant the stent-containing device in a subject.

Although various embodiments are specifically illustrated and described herein, it will be appreciated that modifications and variations of the present disclosure are covered by the above teachings and are within the purview of the appended claims without departing from the spirit and intended scope of the invention.

What is claimed is:

1. A medical device comprising:
a stent body having two ends, a central region therebetween, and comprising structural elements extending around the stent body;
a covering material disposed over the stent body, the covering material covering only a portion of the stent body; and
a bonding material, the bonding material associated with only a portion of the structural elements;
wherein the covering material is provided with a plurality of openings that provide areas where the stent body is not covered by the covering material.

2. The medical device of claim 1, wherein the covering material comprises:
(a) polysiloxanes;
(b) fluoropolymers;
(c) polyamides;
(d) polyesters;
(e) polyurethanes;
(f) polyolefin polymers;
(g) polyoxyalkylenes; or
(h) styrenic copolymers;
(i) any combinations one or more of the foregoing (a)-(h).

3. The medical device of claim 1, wherein the plurality of openings are disposed around a circumference of the stent body.

4. The medical device of claim 1, wherein the bonding material is associated with the structural elements only in areas of the stent body not covered by the covering material.

5. The medical device of claim 1, wherein the bonding material is configured to bond to tissue when the bonding material is exposed to an energy source.

6. The medical device of claim 5, wherein the energy source is selected from a light energy source, a microwave energy source, a radio frequency energy source, infrared energy source, radiation source, and a plasma energy source.

7. The medical device of claim 1, wherein the bonding material is associated with the medical device by integrating the bonding material into at least a portion of the structural elements.

8. The medical device of claim 1, wherein the medical device is self-expanding or balloon-expandable.

9. A method of treatment:
inserting into a body lumen a medical device that comprises a stent body having two ends, a central region therebetween, and comprising structural elements extending around the stent body; a covering material disposed over the stent body, the covering material covering only a portion of the stent body; and a bonding material, the bonding material associated with only a portion of the structural elements, wherein the covering material is provided with a plurality of openings that provide areas where the stent body is not covered by the covering material;
deploying the stent body in the body lumen such that the medical device contacts a tissue wall of the body lumen.

10. The method of claim 9, wherein the covering material comprises:
(a) polysiloxanes;
(b) fluoropolymers;
(c) polyamides;
(d) polyesters;
(e) polyurethanes;
(f) polyolefin polymers;
(g) polyoxyalkylenes; or
(h) styrenic copolymers;
(i) any combinations one or more of the foregoing (a)-(h).

11. The method of claim 9, wherein the plurality of openings are disposed around a circumference of the stent body.

12. The method of claim 9, wherein the bonding material is associated with the structural elements only in areas of the stent body not covered by the covering material and wherein the method comprises bonding the bonding material to the tissue wall.

13. The method of claim 12, wherein bonding the bonding material to the tissue wall comprises exposing the bonding material to an energy source selected from a light energy source, a microwave energy source, a radio frequency energy source, infrared energy source, radiation source, and a plasma energy source.

14. A medical apparatus, comprising: (a) medical device comprising a stent body having two ends, a central region therebetween, and comprising structural elements extending around the stent body; a covering material disposed over the stent body, the covering material covering only a portion of the stent body; and a bonding material, the bonding material associated with only a portion of the structural elements, wherein the covering material is provided with a plurality of openings that provide areas where the stent body is not covered by the covering material; and (b) balloon catheter or a catheter having a retractable sheath configured to deliver the medical apparatus.

15. The medical apparatus of claim 14, wherein the covering material comprises:
(a) polysiloxanes;
(b) fluoropolymers;
(c) polyamides;
(d) polyesters;
(e) polyurethanes;
(f) polyolefin polymers;
(g) polyoxyalkylenes; or
(h) styrenic copolymers;
(i) any combinations one or more of the foregoing (a)-(h).

16. The medical apparatus of claim 14, wherein the plurality of openings are disposed around a circumference of the stent body.

17. The medical apparatus of claim 14, wherein the bonding material is associated with the structural elements only in areas of the stent body not covered by the covering material.

18. The medical apparatus of claim 17, wherein the apparatus further comprises an energy source and wherein the medical device is configured to bond to tissue when the bonding material is exposed to the energy source.

19. The medical apparatus of claim 18, wherein the energy source is selected from a light energy source, a microwave energy source, a radio frequency energy source, infrared energy source, radiation source, and a plasma energy source.

* * * * *